US006325876B1

(12) United States Patent
Adolph et al.

(10) Patent No.: US 6,325,876 B1
(45) Date of Patent: Dec. 4, 2001

(54) ENERGETIC PLASTICIZERS CONTAINING 3,3-BIS(DIFLUOROAMINO)-1,5-DINITRATOPENTANE AND METHOD OF PREPARATION

(75) Inventors: Horst G. Adolph, Warrenton, VA (US); Nirupam J. Trivedi, Laurel, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/516,891

(22) Filed: Mar. 2, 2000

(51) Int. Cl.[7] ......................... C06B 45/10; C07C 203/00; C07C 331/00
(52) U.S. Cl. ........................ 149/19.3; 558/483; 558/485; 558/487
(58) Field of Search ........................ 149/19.3; 558/483, 558/485, 487

(56) References Cited

U.S. PATENT DOCUMENTS

| | | |
|---|---|---|
| 3,190,894 | 6/1965 | Logothetis ........................ 260/396 |
| 3,331,867 | 7/1967 | Smiley ........................... 260/467 |
| 3,337,627 | 8/1967 | Mueller et al. .................. 260/570.5 |
| 3,345,398 | 10/1967 | Rhodes ........................... 260/467 |
| 3,352,914 | 11/1967 | Perry et al. ..................... 260/570.5 |
| 3,375,259 | 3/1968 | Gibson et al. .................... 260/309.7 |
| 3,410,870 | 11/1968 | Armstrong et al. ................ 260/338 |
| 3,729,501 | 4/1973 | Rohrback et al. .................. 260/467 |
| 3,946,085 | 3/1976 | Adolph .......................... 260/615 A |
| 3,968,160 | 7/1976 | Reed, Jr. ....................... 260/584 C |
| 4,001,059 | 1/1977 | Petry ............................ 149/109.4 |
| 4,020,176 | 4/1977 | Greenwald ........................ 260/349 |
| 4,075,246 | 2/1978 | Baum et al. ...................... 260/584 |
| 4,118,414 | 10/1978 | Goldstein et al. ................. 260/467 |
| 4,141,910 | 2/1979 | Flanagan et al. .................. 260/349 |
| 4,341,712 | 7/1982 | Frankel et al. ................... 260/349 |
| 4,376,665 | 3/1983 | Marcellis et al. ................. 149/22 |
| 4,430,514 | 2/1984 | Schack ........................... 564/496 |
| 5,272,249 | 12/1993 | Archibald et al. ................. 528/417 |
| 5,420,311 | 5/1995 | Archibald et al. ................. 549/510 |
| 5,789,617 | 8/1998 | Archibald et al. ................. 564/121 |

*Primary Examiner*—Charles T. Jordan
*Assistant Examiner*—Aileen J. Baker
(74) *Attorney, Agent, or Firm*—Mark Homer

(57) ABSTRACT

A compound has the structure of 3,3-bis(difluoroamino)-1, 5-dinitratopentane and is useful in energetic materials.

11 Claims, No Drawings

ENERGETIC PLASTICIZERS CONTAINING 3,3-BIS(DIFLUOROAMINO)-1,5-DINITRATOPENTANE AND METHOD OF PREPARATION

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention relates to the composition of 3,3-bis(difluoroamino)-1,5-dinitratopentane, abbreviated herein as BFDNP, and the use of BFDNP as a plasticizer in energetic materials. More particularly, 3,3-bis (difluoroamino)-1,5-dinitratopentane is useful as an energetic plasticizer composition in propellants and explosives.

2. Brief Description of the Related Art

Solid propellants containing aluminum or boron fuel exhibit improved metal combustion when fluorine is present as an oxidizer in addition to oxygen. Several patents disclose difluoroamino compounds in energetic compositions. U.S. Pat. No. 3,190,894 to Logothetis discloses 9,10-bis (difluoroamino)-9,10-dihydroanthracenes. U.S. Pat. No. 3,331,867 to Smiley discloses 1,2,5,6-tetrakis (difluoroamino)-3,4-hexanediol dinitrate compounds. U.S. Pat. No. 3,337,627 to Mueller, et al. discloses gem-bis (difluoroamino), 1,3,3-tris(difluoroamino), and 1,1,4,4-tetrakis(difluoroamino) compounds. U.S. Pat. No. 3,345,398 to Rhodes discloses 1,2-bis(difluoroamino) ethane diol-1,2 compounds. U.S. Pat. No. 3,375,259 to Gibson, et al. discloses propellants such as N,N'-bis (difluoroaminomethyl)urea compounds. U.S. Pat. No. 3,410,870 to Armstrong, et al. discloses 2,3-bis(difluoroamino)-1,4-butanediol dinitrate compounds. U.S. Pat. No. 3,729,501 to Rohrback, et al. discloses 1-difluoroamino-2,3-dinitratopropane compounds. U.S. Pat. No. 3,946,085 to Adolph discloses bis(2,2,2-fluorodinitroethyl) trichloroacetal compounds. U.S. Pat. No. 3,968,160 to Reed, Jr. discloses 1,2,3-tris[difluoroamino)ethoxy]-propane compounds. U.S. Pat. No. 4,001,059 to Petry discloses 1-cyano-2,3,5,6-tetrakis(difluoroamino)hexane compounds. U.S. Pat. No. 4,075,246 to Baum, et al. discloses,1,3-bis(2,2,2-fluorodinitroethoxy)-2,2-bis(difluoroamino)propane compounds. U.S. Pat. No. 4,118,414 to Goldstein, et al. discloses tris(difluoroamino)methoxypentaerythrityl trinitrate compounds. U.S. Pat. No. 4,141,910 to Flanagan, et al. discloses 1,7-diazido-4,4-difluoroaminoheptane compounds. U.S. Pat. No. 4,341,712 to Frankel, et al. discloses bis[5,5,5-fluorodinitro-2,2-bis-(difluoroamino)-pentyl]trifluoroacetal (SYTA) compounds. U.S. Pat. No. 4,376,665 to Marcellis, et al. discloses a mixture of pentaborane and tris (difluoroamino)fluoromethane compounds. U.S. Pat. No. 4,430,514 to Schack discloses production of difluoroaminotrifluoromethane compounds. U.S. Pat. No. 5,272,249 to Archibald, et al. discloses bis-(difluoroaminomethyl) oxetanes. U.S. Pat. No. 5,420,311 to Archibald, et al. discloses bis-(difluoroaminomethyl)oxetanes. U.S. Pat. No. 5,789,617 to Archibald, et al. discloses neopentyl difluoroamino compounds.

Other energetic plasticizers, such as 1,2,3 tris(1,2-bis (difluoroamino)ethoxy)propane (TVOPA), 2,2-bis (difluoamino)-5-fluoro-5,5-dinitropentyl formal (SYFO), and 2,2-bis(difluoroamino)-1,3-bis(fluorodinitroethoxy) propane (SYEP) also have been evaluated as plasticizers in aluminized solid propellants. However, TVOPA has limited chemical and thermal stability, and SYFO and SYEP are difficult to manufacture due to laborious, low-yield, multi-step syntheses.

There is a need in the art to provide new difluoroamino compounds for use in energetic compositions. The present invention addresses this and other needs.

SUMMARY OF THE INVENTION

The present invention includes a compound comprising 3,3-bis(difluoroamino)-1,5-dinitratopentane.

The present invention also includes an energetic material comprising 3,3-bis(difluoroamino)-1,5-dinitratopentane.

Furthermore, the present invention further includes a compound of 3,3-bis(difluoroamino)-1,5-dinitratopentane made by the process comprising the steps of difluoroamination and nitration.

DETAILED DESCRIPTION OF THE PREFERRED EMBODIMENT

The present invention is an improved energetic plasticizer containing difluoroamino groups, more specifically the composition of 3,3-bis(difluoroamino)-1,5-dinitratopentane (BFDNP). BFDNP of the present invention can be used as a plasticizer in energetic compositions, such as propellants and explosives. The 3,3-bis(difluoroamino)-1,5-dinitratopentane is manufactured through a process of difluoroamination and nitration.

The compound of 3,3-bis(difluoroamino)-1,5-dinitratopentane of the present invention comprises a structure as shown in formula (I), below:

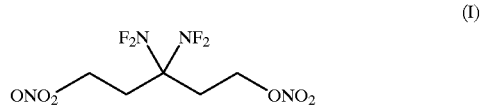

(I)

BFDNP ($O_2NO(CH_2)_2C(NF_2)_2(CH_2)_2ONO_2$) comprises a mobile liquid at room temperature. Differential Scanning Calorimeter (DSC) characterization showed a glass transition temperature of −87° C. and an onset decomposition temperature of 186° C., peaking at 196° C. BFDNP has a density of 1.56 g/cm$^3$. The heat of formation is estimated to be −76 kcal/mol. Based on this data, the performance calculations for BFDNP by the Kamlet Short Method (KSM/GAB) method revealed a Specific Impulse (Isp) of 278.9 seconds. Compared to 262.3 seconds for BTTN, 258.6 seconds for SYFO, and 266.5 seconds for SYEP, BFDNP provides an improved plasticizer with excellent performance potential.

The present invention provides the compound 3,3-bis (difluoroamino)-1,5-dinitratopentane (BFDNP) as an improved energetic plasticizer containing difluoroamino and nitrato groups as oxidizer functions. This compound is synthesized in one embodiment from a known compound of 1,5-dichloropentanone-3 in approximately 3 or 4 steps by replacing the chlorines with trifluoroacetoxy groups; reacting with difluoroamine in oleum; and, replacing the trifluoroacetoxy by nitrato groups either directly or via the parent diol.

The process of manufacturing the 3,3-bis(difluoroamino)-1,5-dinitratopentane comprises the steps of difluoroamination and nitration, as detailed in Examples 1–3, below. As seen in the examples, the step difluoroamination comprises reacting 1,5-bis(trifluoroacetoxy)pentan-3-one ((CF$_3$C(=O)OCH$_2$CH$_2$)$_2$C=O) with difluoroamine reactant, preferably containing oleum, to form 3,3-bis(difluoroamino)-1,5-bis(trifluoroacetoxy)pentane. The 3,3-bis(difluoroamino)-1,5-bis(trifluoroacetoxy)pentane ((CF$_3$C(=O)OCH$_2$CH$_2$)$_2$C(NF$_2$)$_2$) reacted with methanol to form 3,3-bis(difluoroamino)pentanediol-1,5(HO(CH$_2$)$_2$C(NF$_2$)$_2$(CH$_2$)$_2$OH) followed by nitration with a mixture of sulfric acid and nitric acid (H$_2$SO$_4$/HNO$_3$) to form the 3,3-bis(difluoroamino)-1,5-dinitratopentane. In an alternative embodiment, the nitration of 3,3-bis(difluoroamino)-1,5-bis(trifluoroacetoxy)pentane can be directly performed with a mixture of sulfuric acid and nitric acid. In another embodiment, difluoroamination and nitration of the 1,5-bis(trifluoroacetoxy)pentan-3-one is accomplished directly with a difluoroamine reactant in oleum followed by a reaction with nitric acid.

The synthesis of 1,5-dichloropentan-3-one (Cl(CH$_2$)$_2$C(=O)(CH$_2$)$_2$Cl) is known, as described in the Journal of the Chemical Society (C) 1970, 2401 by O. R. Owen and C. B. Reese, the disclosure of which is herein incorporated by reference. Generally a reaction of 3-chloropropionyl chloride (Cl(CH$_2$)$_2$C(=O)Cl), ethylene (CH$_2$=CH$_2$) and aluminum chloride (AlCl$_3$) is performed. The 1,5-dichloropentan-3-one is reacted with sodium trifluoroacetate (NaOC(=O)CF$_3$) to produce 1,5-bis(trifluoroacetoxy)pentan-3-one (CF$_3$C(=O)OCH$_2$CH$_2$)$_2$C=O).

Schematically, the synthesis of the 3,3-bis(difluoroamino)-1,5-dinitratopentane of the present invention may be shown as:

Difluoroamine was generated from a difluorurea solution obtained by fluorination of 13.2 g of urea in 150 mL of water. The difluoroamine was passed into a 3-neck flask fitted with a magnetic stirring bar and a dry-ice condensor and containing 15 mL of 30% oleum and 5 mL of dichloromethane. To the stirred mixture was added gradually a solution of 8 g of crude bis(trifluoroacetoxy)pentanone in 10 mL of dichloromethane. Stirring was continued for 3 hours while the condenser was charged with dry-ice/acetone. The mixture was then poured over crushed ice, the mixture was filtered to remove a brown solid, the phases were separated and the aqueous phase was extracted with dichloromethane. Drying with MgSO$_4$, filtering the solution, and removing the solvent gave 6.5 g of a light brown oil, yielding 62.6% 3,3-bis(difluoroamino)-1,5-bis(trifluoroacetoxy)pentane. Analysis of the 3,3-bis(difluoroamino)-1,5-bis(trifluoroacetoxy)pentane showed 1HNMR (CDCl3, TMS ref.): 2.65 (t, 4H), 4.65 (t, 4H) ppm. 19FNMR (d6-acetone, CFCl3 ref.): +28.94 (NF$_2$), −74.92 (CF$_3$) ppm.

The 3,3-bis(difluoroamino)-1,5-bis(trifluoroacetoxy)pentane (6.5 g), was mixed with 25 mL of anhydrous methanol and the mixture was heated for 2 days at 65° C. The mixture was filtered with suction and freed of solvent in vacuo. 3.86 g of a light brown oil was obtained. The product was triturated with 15 mL of water, then twice with 10 mL of water. The combined aqueous phases were rinsed with 3 mL of dichloromethane. The aqueous solution was saturated with sodium chloride and extracted with 4×25 mL of ether. Work-up of the ether solution as usual gave 1.7 g of a light yellow oil comprising 3,3-bis(difluoroamino)pentanediol-1,5. Additional product of 3,3-bis(difluoroamino)pentanediol-1,5 is contained in the residue of the water trituration, and in the dichloromethane solution used to rinse

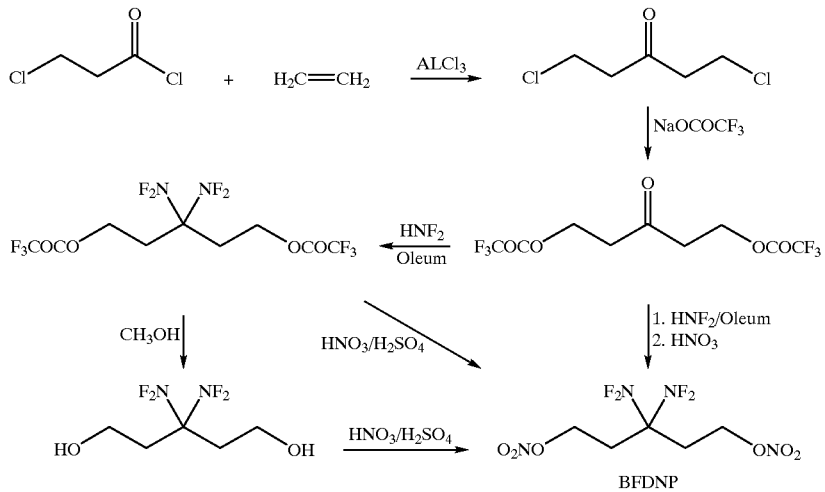

BFDNP

EXAMPLE 1

A mixture of 17.85 g of 1,5-dichloropentan-3-one, 92 mL of trifluoroacetic acid, and 34.55 g of sodium trifluoroacetate was stirred and heated at 75° C. for 64 hours. The mixture was allowed to cool to room temperature, was poured over crushed ice, and a product of 1,5-bis(trifluoroacetoxy)pentan-3-one was extracted with dichloromethane. After drying with MgSO$_4$, filtering, and removal of the solvent, 24.4 g of crude 1,5-bis(trifluoroacetoxy)pentan-3-one product was obtained. Analysis of the 1,5-bis(trifluoroacetoxy)pentan-3-one showed 1HNMR (CDCl3, TMS ref.): 2.94 (t, 4H), 4.63 (t, 4H) ppm.

the aqueous phase. Analysis of the 3,3-bis(difluoroamino)pentanediol-1,5 showed 1HNMR (CDCl3, TMS ref.): 2.46 (t, 4H), 2.95(s, 2H), 3.96(t, 4H) ppm. 19FNMR (d6-acetone, CFCl3 ref.): +27.86 ppm.

A mixture of 1.5 mL of conc. sulfuric acid and 0.7 mL of 100% nitric acid was cooled in an ice bath and 0.7 g of bis(difluoroamino)pentanediol was added with stirring. Stirring with cooling was continued for 2 hours. The mixture was poured over crushed ice and the product was extracted with dichloromethane. The dichloromethane solution was washed with aqueous sodium hydrogen carbonate solution, dried with MgSO$_4$, and filtered. An aliquot was freed of solvent to determine the yield and properties of 3,3-bis (difluoroamino)-1,5-dinitratopentane. The yield was essentially quantitative. Analysis of the 3,3-bis(difluoroamino)-1,5-dinitratopentane showed 1HNMR (CDCl3, TMS ref.): 2.61 (t, 4H); 4.75 (t, 4H) ppm. 19FNMR (d6-acetone, CFCl3 ref.): +29.04 ppm.

EXAMPLE 2 (prophetic)

The 3,3-bis(difluoroamino)-1,5-bis(trifluoroacetoxy) pentane (8.0 g) from example 1 is mixed with 15.0 mL conc. sulfuric acid and 7.0 mL of 100% nitric acid cooled in an ice bath to form 3,3-bis(difluoroamino)-1,5-dinitratopentane.

EXAMPLE 3 (prophetic)

The 1,5-bis(trifluoroacetoxy)pentan-3-one (8.0 g) from example 1 is mixed with 11.6 g difluoroamine in 15 mL of 30% oleum and 5 mL of dichloromethane, followed by mixing with 7.0 mL of 100% nitric acid with cooling in an ice bath to form 3,3-bis(difluoroamino)-1,5-dinitratopentane.

The 3,3-bis(difluoroamino)-1,5-dinitratopentane comprises an energetic material useful as a plasticizer in propellant compositions. Polymers, such as cellulose acetate butyrate (CAB) or plastisol nitrocellulose (PNC), are used in combination with the BFDNP to form the propellant binder. The BFDNP to polymer ratio may be any suitable amount for a given purpose, preferably, from about 1:1 or greater, more preferably from about 1.5:1 or greater, and most preferably from about 2:1 or greater, with the proper amount of energetic material to polymer for a particular purpose determinable by those skilled in the art. Additionally, the BFDNP is useful in explosive compositions.

BFDNP provides a very high energy content, or specific impulse (Isp), due to the high NF fluorine content (26%) with the difluoroamino groups present as a gem-difluoroamino moiety. Additionally, BFDNP is relatively easily synthesized, compared to such compounds as SYFO and SYEP.

The foregoing summary, description, and examples of the present invention are not intended to be limiting, but are only exemplary of the inventive features which are defined in the claims.

What is claimed is:

1. A compound comprising 3,3-bis(difluoroamino)-1,5-dinitratopentane.

2. An energetic material comprising 3,3-bis (difluoroamino)-1,5-dinitratopentane.

3. The energetic material of claim 2, comprising a plasticizer of 3,3-bis(difluoroamino)-1,5-dinitratopentane.

4. A propellant composition comprising the energetic material of claim 3.

5. A propellant composition comprising a polymer selected from the group consisting of cellulose acetate butyrate and plastisol nitrocellulose in combination with the energetic material of claim 3.

6. The propellant of claim 5, wherein the polymer comprises cellulose acetate butyrate.

7. The propellant of claim 5, wherein the polymer comprises plastisol nitrocellulose.

8. The propellant of claim 5, wherein the energetic material is combined with the polymer in a ratio of from about 1:1 or greater.

9. The propellant of claim 8, wherein the energetic material is combined with the polymer in a ratio of from about 1.5:1 or greater.

10. The propellant of claim 9, wherein the energetic material is combined with the polymer in a ratio of from about 2:1 or greater.

11. An explosive composition comprising the energetic material of claim 2.

* * * * *